United States Patent [19]

Mang

[11] Patent Number: 5,371,934
[45] Date of Patent: Dec. 13, 1994

[54] PROCESS FOR MAKING REINFORCED, THIN-WALLED TUBING

[75] Inventor: Warren G. Mang, Haddonfield, N.J.

[73] Assignee: Markel Corporation, Norristown, Pa.

[21] Appl. No.: 14,710

[22] Filed: Feb. 8, 1993

[51] Int. Cl.⁵ .................................................. B23P 17/00
[52] U.S. Cl. .......................................... 29/423; 29/282; 264/573
[58] Field of Search .................. 29/423, 728, 819, 820, 29/282, 559, 281.1; 269/20, 48.1; 264/103, 512, 570, 572, 573

[56] References Cited

U.S. PATENT DOCUMENTS

| | | |
|---|---|---|
| 2,964,796 | 12/1960 | Press .............................. 264/573 X |
| 3,485,234 | 12/1969 | Stevens . |
| 4,093,484 | 6/1978 | Harrison et al. ............... 264/573 X |
| 4,411,055 | 10/1983 | Simpson et al. ................ 264/573 X |
| 4,495,134 | 1/1985 | Ouchi et al. .................... 264/573 X |
| 4,567,917 | 2/1986 | Millard ............................. 138/126 |
| 5,002,559 | 3/1991 | Tower . |

FOREIGN PATENT DOCUMENTS 2584018  1/1987  France ................................. 264/573

Primary Examiner—Mark Rosenbaum
Assistant Examiner—S. Thomas Hughes
Attorney, Agent, or Firm—Synnestvedt & Lechner

[57] ABSTRACT

Methods for reinforcing thin-walled, flexible tubing using pressurized fluids which have excellent mechanical integrity, including burst-strength. The methods comprise pressurizing a tubular conduit with pressurized fluid followed by applying reinforcing means to the conduit.

14 Claims, 1 Drawing Sheet

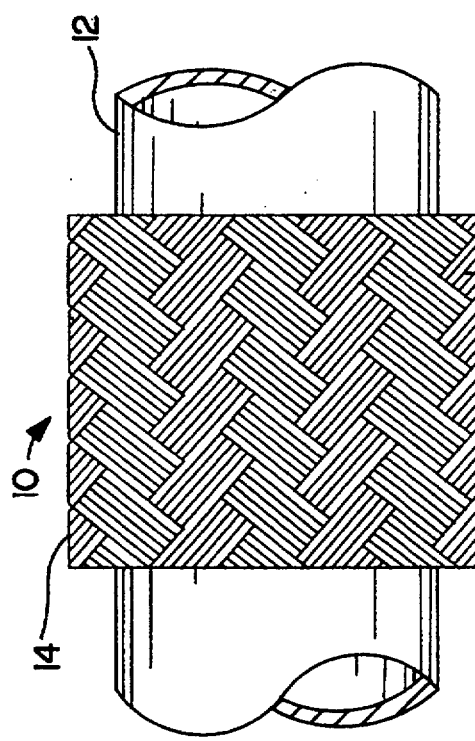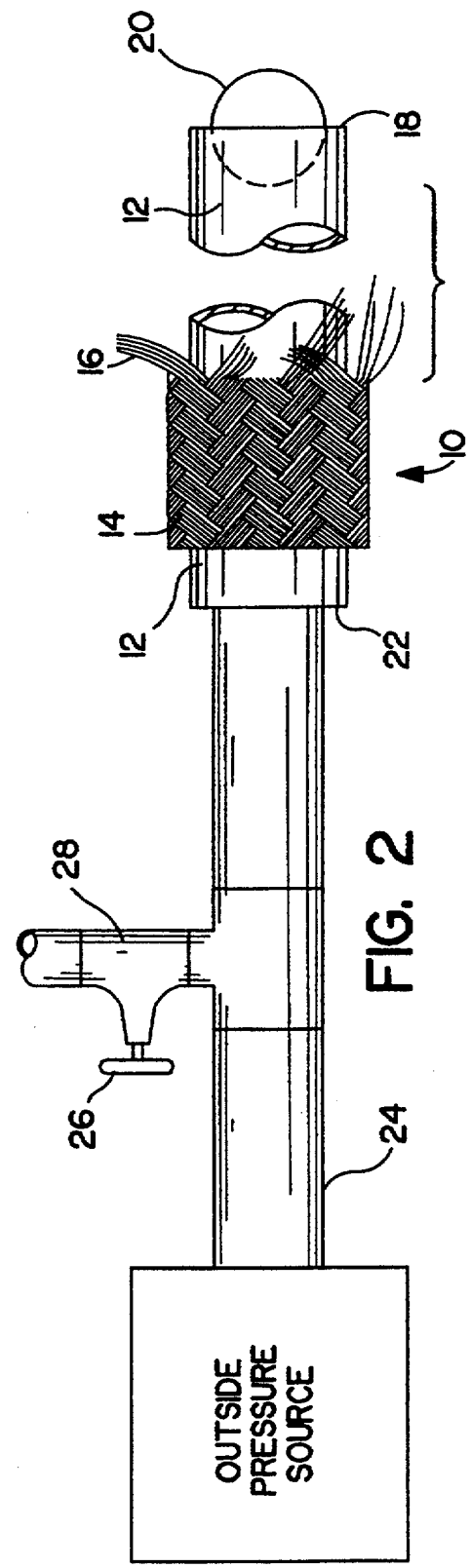

PROCESS FOR MAKING REINFORCED, THIN-WALLED TUBING

FIELD OF THE INVENTION

This invention relates to reinforced tubing. More particularly, this invention relates to methods for producing reinforced thin-walled flexible tubing.

BACKGROUND OF THE INVENTION

Reinforced flexible tubing is used in a variety of important commercial applications. One of the more important applications for such reinforced tubing is in tubular medical devices, for example, catheters. Catheters are generally designed for insertion into canals, vessels, passageways or body cavities so as to permit injection or withdrawal of fluids or other materials. For example, such catheters may be used to introduce medicinal compositions into a patient's bloodstream. In other cases, the catheters may provide a stable, secure passageway for passing solid materials, such as guide wires, angioplasty balloons and stents into a patient's body. In such cases the catheters, which are sometimes referred to as "introducer sheaths," desirably possess a relatively low friction inner surface which facilitates movement of the solid materials through the introducer sheath. In many applications, this low friction inner surface is provided by a relatively thin-walled tubular liner comprised of low friction material.

Catheters are generally engineered to accommodate various, often countervailing, requirements. For example, it is generally required that catheters are flexible and possess good mechanical integrity, including burst-strength. In addition, it is generally required that catheters possess substantially small diameters so that they may be inserted into restricted body passageways, for example, blood vessels. Such small diameter catheters generally comprise an inner surface of substantially thin walled tubing to provide an opening through which fluids or solids are injected or withdrawn. However, such thin-walled tubing is generally prone to bursting and/or mechanical deformation, for example, wall collapse or kinking, resulting in flow reduction or stoppage.

To overcome the tendency of thin-walled catheter tubing to deform mechanically, the tubing is generally reinforced. The reinforcing of such tubing typically comprises covering the tubing with braided coverings which include a plurality of interwoven strands of wires. Such reinforced tubing is disclosed, for example, in U.S. Pat. Nos. 3,485,234; 4,567,917; and 5,002,559, each of which is incorporated herein by reference.

However, reinforcing thin-walled tubing with a covering of woven or braided wires is problematic. For example, the ready deformation of the thin-walled tubing is such that it is generally difficult to maintain the mechanical integrity of the thin-walled tubing while the braided covering is being wound onto or applied to the tubing. Thus, the tubing is subject to deformation during the reinforcement process.

To overcome the problems associated with methods for reinforcing thin-walled tubings, prior art techniques utilize a substantially rigid mandrel which is typically inserted into the tubing prior to the reinforcing process. The mandrel prevents the deformation of the tubing which would otherwise result from the mechanical stresses that occur during the reinforcement process.

However, the technique of inserting a mandrel into the tubing during reinforcing procedures suffers from serious drawbacks. For example, the length of tubing which may be reinforced during any given reinforcing procedure is generally dictated by the length of the mandrel. Thus, reinforcing a substantially long distance of tubing requires a correspondingly long mandrel. The requirement of such long mandrels imposes process limitations and results in increased manufacturing costs. Furthermore, the use of such a solid mandrel is generally very expensive as a result of the stringent tolerance requirements which must be met in order for such a mandrel to effectively reinforce the thin-walled tubing without itself causing destructive deformation of the thin-walled tube.

Accordingly, it is an object of the present invention to provide improved methods for reinforcing thin-walled tubing.

It is a further object of the present invention to provide cost-effective reinforced thin-walled tubing.

It is yet a further object of the present invention to provide methods for reinforcing thin-walled tubing which involve simple processing techniques.

These and other objects of the present invention will become apparent from the detailed description of preferred embodiments which follows.

SUMMARY OF THE INVENTION

One aspect of the present invention relates to methods of reinforcing tubular conduits with reinforcing means, wherein the methods comprise (a) pressurizing the conduit with pressurized fluid medium; and (b) applying the reinforcing means to the conduit while the conduit is pressurized.

BRIEF DESCRIPTION OF THE DRAWING

FIG. 1 is a reinforced tubing assembly according to one embodiment of the present invention.

FIG. 2 is a semi-schematic representation of a reinforced tubing assembly configuration according to one embodiment of the present invention.

DETAILED DESCRIPTION

The methods of the present invention provide cost-effective reinforced tubular conduits for various applications, including medical applications, which have excellent flexibility and mechanical integrity, including burst-strength. The methods of the present invention also provide simple and elegant techniques for reinforcing tubing, including thin-walled tubing.

Referring to the drawing, wherein like numerals refer to like elements, there is illustrated a portion of a reinforced tubular conduit assembly 10 in accordance with the present invention. The assembly 10 includes a flexible tubular conduit 12. In accordance with preferred embodiments of the present invention, the conduit 12 comprises an extruded, substantially inert polymeric material, for example, an inert plastic. Inert plastic materials are particularly preferred in the event that the assembly 10 is used in tubular medical devices, for example, catheters. This substantially prevents any interaction of the assembly 10 with body fluids which therefore may remain inserted in a patient for extended periods of time.

According to preferred embodiments of the present invention, the tubular conduit comprises a fluorocarbon polymer, such as polytetrafluoroethylene. A suitable polytetrafluoroethylene is TEFLON ®, commercially available from DuPont de Nemours Company of Wilmington, Del. Other polymeric materials to be used as the conduit 12 would be readily apparent to one of ordinary skill in the art in view of the present disclosure.

In accordance with preferred embodiments of the present invention, the tubular conduit 12 comprises a substantially thin-walled conduit. As the term is used herein, "thin-walled" refers to conduits having a wall thickness of about 0.004 inch or less. It is generally preferred that the thin-walled conduits of the present invention have a wall thickness of from about 0.001 to about 0.004 inch, with wall thicknesses of from about 0.002 to about 0.004 inch being more preferred and wall thicknesses of about 0.002 inch being even more preferred. Furthermore, it is preferred that the conduits of the present invention are tubular conduits, as is shown in the FIGURE. In such embodiments, it is preferred that the tubular conduit have an outer diameter of from about 0.030 to about 0.250 inch and an inner diameter of from about 0.026 to about 0.246 inch. It is contemplated however, that the methods of the present invention can be adapted to tubing having various dimensions and characteristics.

The conduit assembly 10 further comprises reinforcing means 14 to reinforce the conduit 12. Preferably, the reinforcing means 14 comprises a reinforcing wrap, such as a wrap of metal wire, which may be braided or woven in the form of a plurality of bands or strands, each strand indicated by the reference numeral 16. The strands 16 are preferably braided using conventional techniques, for example, conventional braiding machines. An example of the type of braided reinforcements which are particularly suitable for use in the conduit assemblies of the present invention is described in U.S. Pat. No. 4,567,917 which is incorporated herein by reference.

With particular reference to FIG. 2, there is provided herewith a discussion of the method aspects of the present invention. As noted above, the present methods comprise pressurizing the tubular conduit 12 with a pressurized fluid medium. The term "fluid medium" is used herein to refer to any liquid or gas medium which may be introduced into the tubular conduit 12 and which may be pressurized. Preferably, the fluid medium comprises an inert, non-toxic liquid or gas which may be readily pressurized and removed from the conduit 12. Suitable fluid media to be used in accordance with the method aspects of the present invention include, for example, air, nitrogen, and water.

As is known to those skilled in the art, closed systems are generally required to obtain pressures higher than atmospheric pressures. Accordingly, as shown schematically in FIG. 2, the distal end 18 of the tubular conduit 12 is sealed, preferably with sealing means 20. Sealing means 20 may comprise any means which will provide a fluid seal at the distal end 20 of the tubular conduit 12. Thus, the sealing means 20 preferably provides a gas- and/or liquid-tight seal, for example, air- and/or watertight seals. Preferably, the sealing means 20 is removable from the conduit 12 and may be removed as desired. Examples of suitable sealing means 20 include, for example, removable plugs, and the like. It will be appreciated, of course, that other mechanisms may be used to seal the distal end 18 of conduit 12. In the case of a polymeric tubular conduit, for example, the distal end may be closed upon itself in a meltflow process. In other simple embodiments, the distal end 18 of conduit 12 may be simply folded upon itself or pinched so as to provide a substantial closure of the end.

An external fluid medium source provides a source of the fluid medium. Examples of suitable fluid medium sources include, for example, pressurized gas cylinders, hydraulic pumps, and the like. The external fluid medium source communicates with a proximal end 22 of the tubular conduit 12 via the fluid medium conduit 24. As with the sealing means 20 discussed hereinbefore, the fluid medium conduit 24 provides a seal with the proximal end 22 of the tubular conduit 12 and is readily removed or disconnected from the conduit 12.

In accordance with preferred embodiments of the present invention, the tubular conduit 12 is pressurized with the fluid medium to a pressure which is sufficient to prevent or substantially inhibit mechanical deformation of the tubular conduit 12 during application of the reinforcing means 14. However, the tubular conduit 12 should be pressurized to a pressure less than that which would cause bursting of the tubular conduit 12. For embodiments in which the tubular conduit 12 has an outer diameter of from about 0.030 to about 0.250 inch and a wall thickness of from about 0.002 to about 0.004 inch, the tubular conduit 12 preferably is pressurized to a pressure of from about 60 to about 100 pounds per square inch (hereinafter "psi"). More preferably, such a tubular conduit 12 is pressurized to a pressure of from about 60 to about 90 psi and even more preferably, about 70 psi.

After pressurizing the tubular conduit 12 to a desired pressure, the reinforcing means 14 is applied onto the tubular conduit 12 using techniques well known to those skilled in the art. For example, the tubular conduit 12 may be run through a conventional wire braiding machine to form a tightly overlying braided sheath. Methods and apparatus for making braided wire reinforcement are described, for example, in U.S. Pat. Nos. 4,567,917 and 5,085,121, each of which is incorporated herein by reference.

It is contemplated that in accordance with the present invention, the reinforcing means 14 is applied to the tubular conduit 12 while the conduit 12 comprises a planar configuration. For example, the tubular conduit 12 may be uncoiled and situated in a substantially horizontal position during application of the reinforcing means 14. Alternatively, the tubular conduit may be coiled or wound on a spool. In this case, the conduit 12 is accessed by unwinding the conduit 12 from the spool as additional length of the conduit 12 is desired.

In accordance with the present invention, a desired length of the tubing conduit 12 is reinforced with the reinforcing means 14. The length of the tubular conduit 12 to be reinforced with the reinforcing means 14 may vary, and depends, for example, on the desired application of the reinforced tubular conduit assembly 10. Similarly, the length of the reinforcing means 14 to be applied to the tubular conduit 12 may vary and depends on various factors, including the desired application of the assembly 10.

After the desired length of the reinforcement 14 has been applied to the desired length of the tubular conduit 12, valve 26 is opened to release the pressurized fluid medium through the outlet means 28. Thus, in preferred embodiments which involve pressurizing the tubular conduit 12 with inert gas, for example, air, the valve 26 is opened to release the pressurized air which escapes through the outlet means 28. The pressure within the tubular conduit 12 subsequently returns to normal pressures, for example, atmospheric pressure. The sealing means 20 and conduit 24 may then be removed from the reinforced tubular conduit assembly 10. The assembly 10 possesses pressurization and burst-pressure characteristics similar to those characteristics of reinforced conduits prepared according to the prior art.

The methods of the present invention thus provide simple and elegant procedures to prepare cost-effective tubular conduit assemblies which have excellent flexibility and mechanical integrity, including burst-strength.

I claim:

1. A method of reinforcing a thin-walled conduit with reinforcing means, said method comprising:
   (a) providing a thin-walled conduit having a wall thickness of about 0.004 inch or less;
   (b) pressurizing said thin-walled conduit with pressurized fluid medium to a pressure of from about 60 to about 100 psi; and
   (c) applying said reinforcing means to said thin-walled conduit while said thin-walled conduit is pressurized.

2. The method according to claim 1 wherein said conduit comprises a tubular conduit.

3. The method according to claim 2 wherein said conduit comprises a polymeric material.

4. The method according to claim 3 wherein said conduit comprises polytetrafluoroethylene.

5. The method according to claim 1 wherein said reinforcing means comprises metal wire reinforcement.

6. The method according to claim 5 wherein said metal wire reinforcement comprises a plurality of braided strands.

7. The method according to claim 1 wherein said fluid is pressurized air.

8. The method according to claim 7 wherein said fluid comprises pressurized water.

9. The method of claim 2 wherein said conduit comprises an outer diameter of about 0.030 to about 0.250 inch and an inner diameter of about 0.026 to about 0.246 inch.

10. The method according to claim 1 comprising pressurizing said conduit to a pressure of from about 60 to about 90 psi.

11. The method according to claim 10 comprising pressurizing said conduit to a pressure of about 70 psi.

12. The method according to claim 1 wherein said conduit comprises a wall thickness of about 0.001 to about 0.004 inch.

13. The method of claim 12 wherein said conduit comprises a wall thickness of about 0.002 to about 0.004 inch.

14. The method of claim 13 wherein said conduit comprises a wall thickness of about 0.002 inch.

* * * * *